United States Patent
Prescott et al.

(10) Patent No.: US 6,939,538 B2
(45) Date of Patent: Sep. 6, 2005

(54) EXTENDED RELEASE ANALGESIC FOR PAIN CONTROL

(75) Inventors: Albert Prescott, Groton, MA (US); Edward Kislauskis, Medway, MA (US); Dennis L. Guberski, Rutland, MA (US)

(73) Assignee: Biomedical Research Models, Inc., Worcester, MA (US)

( * ) Notice: Subject to any disclaimer, the term of this patent is extended or adjusted under 35 U.S.C. 154(b) by 32 days.

(21) Appl. No.: 10/410,940

(22) Filed: Apr. 10, 2003

(65) Prior Publication Data

US 2003/0194438 A1 Oct. 16, 2003

Related U.S. Application Data

(60) Provisional application No. 60/371,790, filed on Apr. 11, 2002.

(51) Int. Cl.$^7$ .................. A61K 31/535; A61K 31/74
(52) U.S. Cl. ................... 424/78.08; 514/231.2
(58) Field of Search ............. 424/78.08; 514/231.2

(56) References Cited

U.S. PATENT DOCUMENTS 5,275,820 A * 1/1994 Chang .................. 424/426
6,391,336 B1 * 5/2002 Royer .................. 424/468

FOREIGN PATENT DOCUMENTS

JP      07196510    *   8/1995

OTHER PUBLICATIONS

Matsumoto et al, Pharmaceutical evaluation of hollow-type suppositories, 1995, Pharmaceutical Society of Japan, vol. 18 No. 12, pp. 1744–1749.*

* cited by examiner

*Primary Examiner*—Alton Pryor
(74) *Attorney, Agent, or Firm*—Pierce Atwood; Kevin M. Farrell

(57) ABSTRACT

An extended release analgesic for controlling pain comprised of an opioid or non-opioid analgesic drug ionically bound to hyaluronic acid, poly-γ-glutamic acid or other ionic polymers, and injected into a body either subcutaneously, intramuscularly or intraperitoneally, utilizing counter-ions of different valences to control the rate of release into the body.

26 Claims, 3 Drawing Sheets

Key: Standard aqueous morphine sulfate: Asterisks with thin solid line.
Ferric hyaluronate with morphine sulfate: Plus signs with thin solid line.
Sodium polyglutamate with morphine sulfate: "X" with dotted line.
Sodium hyaluronate with morphine sulfate: Squares with dashed line.
Calcium hyaluronate with morphine sulfate: Triangles with bold solid line.

Key: Aqueous morphine sulfate: triangles with dotted line.

Calcium (<1 mg/ml) hyaluronate with morphine sulfate: Asterisks with dashed line.

Calcium (>2 mg/ml) hyaluronate: "X" with bold solid line.

Key: Control Group (no drugs): Squares with bold solid line.

Aqueous morphine sulfate: Triangles with dotted line.

Calcium (<1 mg/ml) hyaluronate: Asterisks with dashed line.

Calcium (>2mg/ml) hyaluronate: "X" with bold solid line.

EXTENDED RELEASE ANALGESIC FOR PAIN CONTROL

CROSS REFERENCE TO RELATED APPLICATION

This application claims priority of Provisional application Ser. No. 60/371,790, filed on Apr. 11, 2002.

FIELD OF THE INVENTION

This invention relates to extended release analgesic for pain control.

BACKGROUND OF THE INVENTION

Analgesics are used to control pain in various situations such as post surgical, post injury, cancer treatment, AIDS treatment and more. Analgesics used include steroidal, non-steroidal, opioid, and non-opioid analgesics. Many of these drugs have very short residence times in the body, ranging from 6 to 12 hours for steroids and non-steroids, to as low as 1 to 3 hours for opioids. Pain from the procedures described can last several days. These analgesics thus must be administered many times in order to be effective in controlling pain.

There are several methods for extending the time over which analgesics are effective. One is advanced chemical entities. Whereas analgesics such as morphine have a mean residence time of only a few hours, advanced synthetic analgesics such as OxyContin® have an effective residence time in the body of 8 hours. Some drawbacks to this material are the fact that it is orally delivered, and as a result the unit dose may be improperly modified by a patient, resulting in a dangerous overdose, or the patient may not be capable of swallowing the medication.

Another method for extending the effective time of analgesics is to meter them into the body via a trans-dermal patch. This method has the advantage of extending the release of analgesics to several days. The drawbacks to this method are that it is external to the body, and thus it may still be manipulated by the patient. For example, some of the patients are pets who scratch at and eat the patches. Another drawback is that the patches are both species and body weight specific. A patch used on a person cannot be used on a dog, and a dog patch may not be used on a cat. Different types of patches must be used for people of different body weights, etc.

SUMMARY OF THE INVENTION

Given the state of the art, there is a definite need for a novel method of analgesic release where, (1) the release of analgesic is measured in days, (2) the release of the analgesic can not be manipulated by the patient or other external sources, (3) fine motor control, such as swallowing, is not required to administer the analgesic, and (4) the amount of analgesic administered is determined by the doctor or nurse depending on the patients' needs (weight, species, etc).

The invention features an analgesic drug ionically bound to an ionic polymer. The polymer may be hyaluronic acid, poly-γ-glutamic acid, or another ionic polymer. The polymer may be anionic, in which case the drug would be cationic, or the polymer may be cationic and the drug anionic. The polymer-drug matrix is injected either subcutaneously, intramuscularly, or intraperitoneally. The matrix is degraded over time via the enzymatic machinery of the body, thus releasing the drug. The rate at which the polymer matrix is degraded by the body may be modified be using various counter-ions in the polymer matrix. Counter cations used can include sodium ($Na^{1+}$), calcium ($Ca^{2+}$), and the ferric form of iron ($Fe^{3+}$), and counter anions used can include chloride ($Cl^{1-}$) and sulfate ($SO_4^{2-}$). The greater the valence on the counter-ion, the slower the polymer matrix will degrade. This is because higher valence ions provide better electrostatic shielding of the polymer's ionic sites, and hence the hydrodynamic radius decreases, inhibiting access of enzymes to the polymer degradation sites. This invention may be administered by a doctor or nurse who has the ability to modify the actual dose to allow for differences in species and body weight.

BRIEF DESCRIPTION OF THE DRAWINGS

Other objects, features and advantages will occur to those skilled in the art from the following description of the preferred embodiments, and the accompanying drawings, in which.

DETAILED DESCRIPTION OF THE PREFERRED EMBODIMENTS

Figure 1:
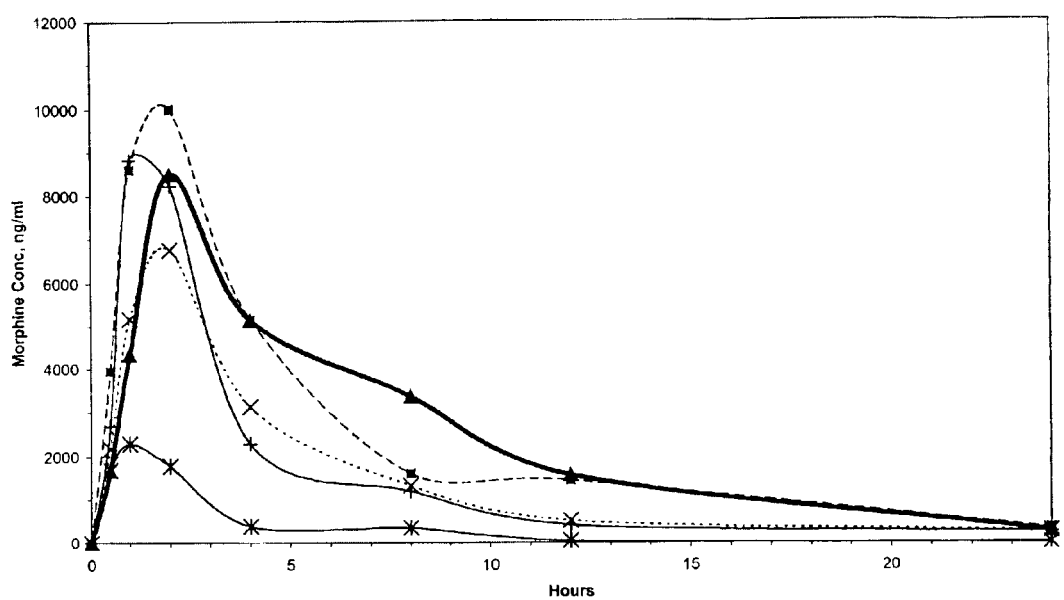
FIG. 1 is a graph of blood morphine concentrations over time resulting from the injection of aqueous morphine sulfate, and several extended release compounds of the invention.

The following is a description of the preferred embodiment of the invention. The preferred polymer is hyaluronic acid having an average molecular weight of over 1 million Daltons. Purified sterile polymer that is pyrogen free is placed in a clean environment (class 100 or cleaner). The amount of analgesic required for the duration of treatment is weighed out and dissolved in sterile saline for injection. The solution is then sterile filtered since the analgesic powder was not sterile. The polymer is then added and the material is mixed for 24 hours, or until all polymer is dissolved. All beakers, stirbars and instruments were sterilized via autoclaving prior to product contact.

In the following examples, four prototypes were tested to determine the release rates for the various conditions explained. These prototypes were formulated as follows:

EXAMPLE 1

Sodium hyaluronate with morphine: All work was performed in a class 100 clean hood. 54 mg of morphine hexahydrate was placed in a depyrogenated beaker. 3 ml of sterile saline (0.9% NaCl) was added to the morphine and swirled until it was dissolved. The solution was then drawn up into a syringe. The syringe was fitted with a sterilizing filter, and the solution was passed through the filter into a clean sterile beaker. 45 mg of sterile and pyrogen free hyaluronic acid was weighed, and placed in the beaker with the solution. The hyaluronic acid had a molecular weight in excess of 1 million Daltons. A sterilized stir-bar was placed in the beaker, and the solution was stirred for 24 hours. The solution was then placed in syringes (1 ml per syringe) and stored for subsequent animal tests.

EXAMPLE 2

Calcium hyaluronate with morphine: All work was performed in a class 100 clean hood. 54 mg of morphine hexahydrate was placed in a depyrogenated beaker. 2.25 ml of sterile water was added to the morphine and swirled until it was dissolved. The solution was then drawn up into a syringe. The syringe was fitted with a sterilizing filter, and the solution was passed through the filter into a clean sterile beaker. 45 mg of sterile and pyrogen free hyaluronic acid was weighed, and placed in the beaker with the solution. The hyaluronic acid had a molecular weight in excess of 1 million Daltons. A sterilized stir-bar was placed in the beaker, and the solution was stirred for 24 hours. 0.0135 grams of calcium chloride was added to 0.75 ml of water, and swirled until dissolved. The solution was then drawn into a syringe, the syringe fitted with a sterile filter, and the solution was added via this sterile filter to the polymer solution. The final solution was then placed in syringes (1 ml per syringe) and stored for subsequent animal tests.

EXAMPLE 3

Ferric hyaluronate with morphine: All work was performed in a class 100 clean hood. 54 mg of morphine hexahydrate was placed in a depyrogenated beaker. 2.25 ml of sterile water was added to the morphine and swirled until it was dissolved. The solution was then drawn up into a syringe. The syringe was fitted with a sterilizing filter, and the solution was passed through the filter into a clean sterile beaker. 45 mg of sterile and pyrogen free hyaluronic acid was weighed, and placed in the beaker with the solution. The hyaluronic acid had a molecular weight in excess of 1 million Daltons. A sterilized stir-bar was placed in the beaker, and the solution was stirred for 24 hours. 0.010 grams of ferric chloride was added to 0.75 ml of water, and swirled until dissolved. The solution was then drawn into a syringe, the syringe fitted with a sterile filter, and the solution was added via this sterile filter to the polymer solution. A sterile solution of 1M NaOH was used to neutralize the solution, which becomes acid when the ferric chloride is added. The solution was then placed in syringes (1 ml per syringe) and stored for subsequent animal tests.

EXAMPLE 4

Sodium poly-γ-glutamate with morphine: Same materials and procedures as #1, except using poly-γ-glutamic acid instead of hyaluronic acid.

Table 1 shows the effect of the use of the sustained release preparations detailed above when injected into rats. Time duration was measured using observation of rat mobility.

TABLE 1

| Material injected | Time duration of analgesic effects |
| --- | --- |
| Aqueous Morphine, control | 2 hours |
| Sodium hyaluronate and morphine | 8 hours |
| Calcium hyaluronate and morphine | >12 hours |
| Ferric hyaluronate and morphine | >12 hours, with onset delayed by 2 hours |
| Sodium poly-γ-glutamic acid and morphine | >6 hours, with onset delayed by 2 hours |

FIG. 1 shows the blood morphine concentrations resulting from the injection of aqueous morphine sulfate, and several extended release compounds made by the processes described above. All formulas had an identical morphine concentration of 18 milligrams of morphine pentahydrate per milliliter. There are several conclusions to be drawn from FIG. 1. First, all the non-aqueous polymer formulas have a longer release of morphine than the standard aqueous dose. Second, the sodium hyaluronate formula has a very high initial peak, followed by a very fast decline of morphine in the blood stream. Third, calcium hyaluronate has a lower peak than both the sodium hyaluronate and the ferric hyaluronate. In addition, it has an elevated "shoulder" between the times of 5 and 12 hours that the other formulas do not have. This is unique because one would have predicted the ferric formula to be more closely packed than the calcium formula, resulting in a slower initial release, followed by elevated levels after the peak, due to its higher valence than calcium. The data, however, contradict this theory because the calcium formula exhibited a slower release than the ferric formula.

Figure 2:
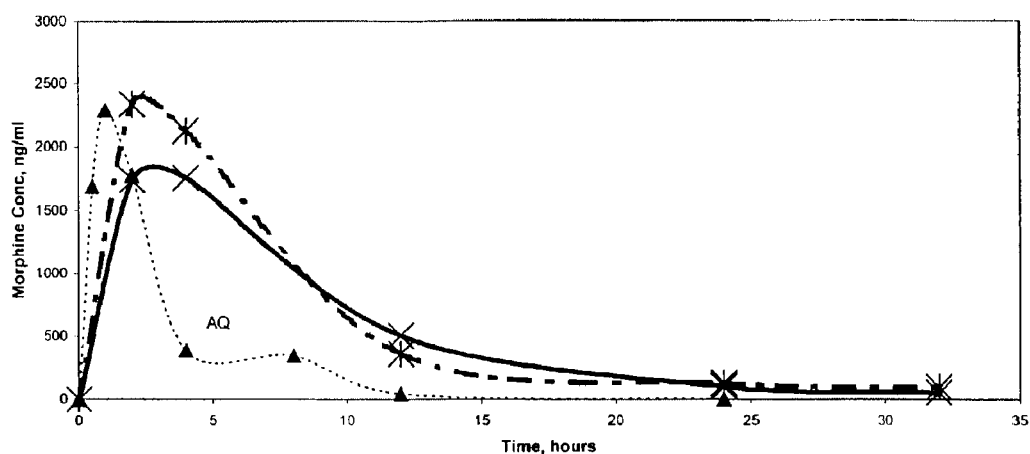
FIG. 2 is a graph of blood morphine concentrations resulting from the injection of aqueous morphine sulfate, and two different extended release compounds of the invention using different amounts of calcium as the counter-ion.

FIG. 2 shows the blood morphine concentrations resulting from the injection of aqueous morphine sulfate, and two extended release compounds of the invention. The purpose of this experiment was to expand the knowledge of the effects of the divalent cation calcium ($Ca^{2+}$) on hyaluronic acid and morphine release. The data clearly shows that increasing the concentration of calcium, results in a lower maximum peak, and a higher "shoulder". This is a very beneficial kinetic for extended release drug delivery.

Figure 3:
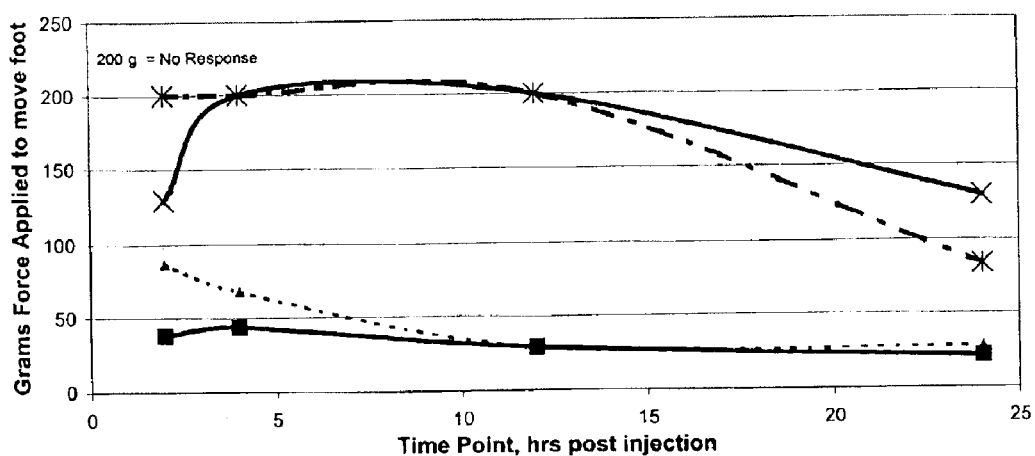
FIG. 3 is a graph showing the pain control effect of the two different inventive compounds also reflected in FIG. 2.

The rats injected with the compounds of FIG. 2 were also tested using an Electrovon frey Analgesiometer to asses their pain response. Each rat had an incision made on one of its hind paws. The amount of force required to illicit a response (rat raises its paw) was measured. The more force required, the greater the analgesia. The results are in FIG. 3. This graph clearly shows that the formula with the most calcium also provides the longest lasting pain control.

Non-opioids for Controlled Release

A person skilled in the art, will understand that the extended release demonstrated for morphine, will also have implications for other opioid drugs such as codeine and oxycodone, as well as non-opioid drugs. Morphine sulfate is comprised of two morphine groups ionically associated with a sulfate group. In solution, the morphine groups are free floating and each have a molecular weight of 285 Daltons.

Three typical non-opioid analgesics comprise acetaminophen (4'-hydroxyacetanilide), acetylsalicylic acid (aspirin), and ibuprofen. Each of these molecules is similar to morphine both structurally (each contains at least one unsaturated aromatic ring), and each is a small molecular weight species, having a range of molecular weights from 130 for acetaminophen to over 200 for ibuprofen. Since these non-opioid molecules are similar to morphine, the release properties for these molecules out of the ionic polymer/counter ion matrix of the invention is expected to be similar to that of morphine.

What is claimed is:

1. A sustained release preparation, comprising:
    a) a negatively charged ionic polymer compound selected from the group consisting of hyaluronic acid and polyglutamic acid;
    b) a calcium counterion; and
    c) a pharmacologically effective amount of at least one ionic analgesic compound wherein the analgesic compound is an opioid.

2. The sustained release preparation of claim 1, wherein the opioid is morphine.

3. The sustained release preparation of claim 1 wherein the analgesic preparation has a pain relieving effect for over 12 hours.

4. The sustained release preparation of claim 3 wherein the analgesic preparation has a pain relieving effect for at least 24 hours.

5. A sustained release preparation, comprising:
   a) the negatively charged ionic polymer compound hyaluronic acid;
   b) a calcium counterion; and
   c) a pharmacologically effective amount of at least one ionic analgesic compound wherein the analgesic compound is an opioid.

6. The sustained release preparation of claim 5, wherein the opioid is morphine.

7. The sustained release preparation of claim 5, wherein the ionic polymer compound hyaluronic acid has an average molecular weight of over one million Daltons.

8. The sustained release preparation at claim 5 wherein the analgesic preparation has a pain relieving effect for over 12 hours.

9. The sustained release preparation of claim 8 wherein the analgesic preparation has a pain relieving effect for at least 24 hours.

10. A sustained release preparation, comprising:
    a) the negatively charged ionic polymer compound polyglutamic acid;
    b) a counterion selected from the group consisting of sodium, calcium and iron; and
    c) a pharmacologically effective amount of at least one ionic analgesic compound wherein the analgesic compound is an opioid.

11. The sustained release preparation of claim 10, wherein the opioid is morphine.

12. The sustained release preparation of claim 10 wherein the analgesic preparation has a pain relieving effect for over 12 hours.

13. A method for effecting sustained release of an analgesic compound in an animal, the method comprising:
    a) providing a sustained release preparation, comprising:
       i) a negatively charged ionic polymer compound selected from the group consisting of hyaluronic acid and polyglutamic acid;
       ii) a calcium counterion; and
       iii) a pharmacologically effective amount of at least one ionic analgesic compound wherein the analgesic compound is an opioid; and
    b) administering the preparation of step a) to the animal.

14. The method of claim 13 wherein the opioid is morphine.

15. The method of claim 13 wherein the analgesic preparation has a pain relieving effect for over 12 hours.

16. The method of claim 15 wherein the analgesic preparation has a pain relieving effect for at least 24 hours.

17. A method for effecting sustained release of an analgesic compound in an animal, the method comprising:
    a) providing a sustained release preparation, comprising:
       i) the negatively charged ionic polymer compound hyaluronic acid;
       ii) a calcium counterion; and
       iii) a pharmacologically effective amount of at least one ionic analgesic compound wherein the analgesic compound is an opioid; and
    b) administering the preparation of step a) to the animal.

18. The method of claim 17 wherein the opioid is morphine.

19. The method of claim 17 wherein the ionic polymer compound hyaluronic acid has an average molecular weight of over one million Daltons.

20. The method of claim 17 wherein the analgesic preparation has a pain relieving effect for over 12 hours.

21. The method of claim 20 wherein the analgesic preparation has a pain relieving effect for at least 24 hours.

22. A method for effecting sustained release of an analgesic compound in an animal, the method comprising:
    a) providing a sustained release preparation, comprising:
       i) the negatively charged ionic polymer compound polyglutamic acid;
       ii) a counterion selected from the group consisting of sodium, calcium and iron; and
       iii) a pharmacologically effective amount of at least one ionic analgesic compound wherein the analgesic compound is an opioid; and
    b) administering the preparation of step a) to the animal.

23. The method of claim 22 wherein the opioid is morphine.

24. The method of claim 22 wherein the analgesic preparation has a pain relieving effect for over 12 hours.

25. A sustained release preparation comprising:
    a) a negatively charged ionic polymer compound;
    b) an iron counterion; and
    c) a pharmacologically effective amount of at least one ionic analgesic compound, wherein the analgesic compound is an opioid.

26. A method for effecting sustained release of an analgesic compound in an animal, the method comprising:
    a) providing a sustained release preparation comprising:
       i) a negatively charged ionic polymer compound;
       ii) an iron counterion; and
       iii) a pharmacologically effective amount of at least one ionic analgesic compound wherein the analgesic compound is an opioid; and
    b) administering the preparation of step a) to the animal.

* * * * *